United States Patent [19]

Ford, Jr.

[11] Patent Number: 4,571,081
[45] Date of Patent: Feb. 18, 1986

[54] LIGHT SCATTERING APPARATUS AND METHOD

[75] Inventor: Norman C. Ford, Jr., Amherst, Mass.

[73] Assignee: Coulter Electronics of New England, Inc., Hialeah, Fla.

[21] Appl. No.: 415,581

[22] Filed: Sep. 7, 1982

[51] Int. Cl.$^4$ .............................................. G01B 9/02
[52] U.S. Cl. .................................... 356/349; 73/64.4; 356/338; 356/344
[58] Field of Search ...................... 356/35.5, 338, 344, 356/349, 354; 73/64.4

[56] References Cited

U.S. PATENT DOCUMENTS 3,090,229  5/1963  Chisholm .............................. 356/354

OTHER PUBLICATIONS

Josefowicz et al., "Homodyne Electrophoretic Light Scattering . . . " *Applied Optics*, vol. 14, No. 3, pp. 740–742.
Hood et al., "Laser Heterodyne Apparatus for Measurement . . . " *J. Appl. Phys.*, vol. 47, No. 6, pp. 2433–2442, 6/76.
Byrne et al., "Photon Correlation Spectroscopy of Liquid Interfaces" . . . *J. Phys. D.*, vol. 2, pp. 1133–1144, 1979.

*Primary Examiner*—Davis L. Willis
*Assistant Examiner*—Matthew W. Koren
*Attorney, Agent, or Firm*—Andrew F. Kehoe

[57] ABSTRACT

A light scattering interfacial tension spectrometer has a laser source of light directed, as an incident beam $I_i$, through a focusing lens and a diffraction grating. The grating divides the incident beam $I_i$ into a main beam $I_m$, undiffracted light, and a higher order, diffracted light, reference beam $I_r$. The beam $I_r$ is passed through an attenuator and a diffraction focusing lens to a region under test, such as a liquid surface. The main beam $I_m$, from the grating is transmitted through the common diffraction focusing lens to the test region where it is reflected. The reference beam $I_r$ is reflected from the test surface together with scattered light $I_s$, and directed through an aperture to a photomultipler tube. The output of the photomultiplier is coupled to a pulse amplifier-discriminator and a photon correlator. For a liquid surface under test the output of the spectrometer provides a measure of the surface tension and the viscosity of the liquid.

17 Claims, 3 Drawing Figures $\lambda$ = ms $\Delta y$ CHANNEL NUMBERS
$\Delta\lambda$ = /ms

LIGHT SCATTERING APPARATUS AND METHOD

FIELD OF THE INVENTION

The present invention relates to apparatus and method for using light scattering techniques for measuring the surface tension and viscosity of a liquid.

BACKGROUND OF THE INVENTION

Devices and techniques for measuring the surface tension and viscosity of fluids in the past have generally been characterized as invasive. Because of the techniques, which are essentially mechanical, the liquid under study is directly affected by the techniques, thereby introducing undesirable artifacts. Such apparatus and techniques are not useful at all for hostile environments such as extremely high temperatures or extremely high pressures or both.

PRIOR ART

More recently a technique which has become known as photon correlation spectroscopy (PCS) has been applied to determine the surface tension and viscosity of liquids by noninvasively studying the thermally excited capillary waves on a liquid surface. The technique generally involves the use of a light divider to generate a local oscillator for use with a photon correlator.

The early use of light scattering at interfacial fluid regions is described in:

Reference 1: "Laser Heterodyne Apparatus for Measurements of Liquid Surface Properties—Theory and Experiments" authored by S. Hard, Y. Hamnerius and O. Nilsson. The paper appears in the Journal of Applied Physics, Vol, 47, No. 6, June, 1976.

Reference 2: The PCS technique is further described in an article by D. Byrne and J. C. Earnshaw entitled "Photon Correlation Spectroscopy of Liquid Interfaces: I. Liquid-Air Interfaces," which appeared in the Journal of the Institute of Physics, Vol 12, 1979.

Both of these papers are hereby incorporated by reference as an integral part of this specification.

Both systems described in the above-referenced articles use a laser light source focused through a spatial filter. The spatial filter aperture is imaged by another lens on the surface of the fluid under test. The reflected and scattered light from the surface of the fluid are passed through a diffraction grating and the scattered light and the diffracted, reflected light are directed through an aperture to a photomultiplier tube. In Byrne, the output of the photomultiplier is then amplified and applied through a discriminator to a photon correlator.

Both of these systems suffer from a significant defect in that the path lengths of the incident beam, the diffracted reference beam and the scattered light are not the same. This results in degradation of the signal characterized by increased noise level, lower sensitivity and resolution.

In both Härd and Byrne, as shown in Byrne's FIG. 4 and Härd's FIG. 1, the grating is positioned between the liquid surface and the photodetector. Byrne, in particular, notes in his Section 3.1 Gratings, that:

"The grating was located very close (2-3 centimeters) to the liquid surface."

He further notes that:

"The grating was mounted with translational and rotational degree of freedom permitting it to be set normal to the specularly reflected beam and as close to the surface as possible."

It will be apparent that with the apparatus of Härd and Byrne, it is impossible to retain coherence of the specularly reflected diffracted and the scattered light because of the inherent differences in light path lengths.

That Byrne fully comprehended this problem is underscored by his comment with respect to his description of his apparatus:

"Only the scattered light spatially coherent with the reference beam beats with it; the remainder can only form a homodyne contribution."

Since the homodyne contribution produces a zero beat frequency, the desired beat signals is degraded to the extent of the homodyne contribution. This has the effect of distorting the correlation functions shown in Byrne, FIG. 5, without the homodyne contribution.

In accordance with the concept of the instant invention the diffraction grating is positioned in such a manner as to image it on the surface of the fluid, thereby effectively positioning a non-invasive phantom grating coincident with the fluid surface.

BRIEF DESCRIPTION OF THE INVENTION

In accordance with a preferred embodiment of the invention, a light scattering interfacial tension spectrometer is designed to be used in photon correlation spectroscopy of fluid interfaces.

The spectrometer has a laser source of light directed through a focusing lens and a diffraction grating. The grating divides the incident beam $I_i$ into a main beam $I_m$, undiffracted light, and a higher order, diffracted light, reference beam $I_r$. The beam $I_r$ is passed through an attenuator and a common diffraction focusing lens to a region under test, such as a liquid surface. The main beam $I_m$, from the grating is transmitted through the common diffraction focusing lens to the test region where it is reflected. The reference beam $I_r$ is reflected from the test surface together with the scattered light $I_s$, and directed through an aperture to a photomultiplier tube.

OTHER APPLICATIONS

The use of PCS in the manner of the present invention is applicable to determinations of the electric charge on microparticles in electrophoresis, the sizes and shapes of macromolecules in solution, the velocity and turbulence at various points in a flowing fluid, and the surface tension and viscosity of a fluid from the interfacial regions. The interfacial regions are fluid to fluid and may be liquid-vapor or liquid-liquid.

In the context of electrophoresis, the system is generally applicable to the determination of charge of particles in the range from 0.01-10 microns or greater. It is especially useful for larger particles on the order of 10 microns.

An important aspect of the invention is the inherent ability to image the dividing means, e.g., the diffraction grating at a selected plane associated with the region under test. For the purpose of determining surface tension and viscosity of a liquid, the dividing means is imaged on the surface of the liquid.

For other purposes, such as electrophoresis, the dividing means is imaged within the liquid in a manner unavailable to prior art method. The dividing means may be a beam splitter or other devices known in the art which need not effect a frequency change in the spatially displaced light.

PCS, in accordance with the invention, presents striking benefits over the prior art in that nondestructive, i.e., noninvasive, remote sensing of the measurement of the interfacial tension and viscosity of a fluid interface may be easily and quickly obtained. Because of this noninvasive property, the measurement may be made in extremely hostile environments involving extraordinarily high pressures and temperatures. The apparatus and method of the invention enable substantially greater accuracy in measuring the surface tension and viscosity. The signal to noise ratio, the sensitivity and the resolution of the signals are greatly enhanced.

As used herein the term "light" includes, but is not limited to, electromagnetic radiation in all of its frequency ranges, including that portion which ranges from the far infrared to the far untraviolet, in addition to the visible.

The term electromagnetic radiation, as used herein, includes all radiation characterized by frequency, phase, coherence and beam forming properties such that, in the sense of the present invention, the radiation has properties substantially equivalent to that described herein. Thus, e.g., sonic and ultrasonic radiation are included.

PROPERTIES OF LIQUID SURFACES

One of the significant distinguishing characteristics of liquids, relative, e.g., to gases, is that they retain their volume and do not fill the space available. This behavior is attributed to the existence of strong, short range attractive forces between the liquid molecules. Beneath the surface of the liquid each molecule is surrounded by other molecules on all sides and therefore the net sum of the attractive forces upon an individual molecule is zero. However, molecules on the surface of the liquid are subjected to an asymmetric net force due to the attraction by the bulk of the liquid. In response to this force, the surface of a liquid contracts until it contains the minimum number of molecules possible. Thus the surface layer is in a state of tension in comparison to the liquid interior. A measurement of the liquid's surface tension is a measure of this force.

The liquid surface is not a static boundary. At any temperature above absolute zero, random thermal processes generate surface fluctuations. Each thermal event at the surface produces waves of low amplitude and in a broad range of wavenumbers. There exist restoring forces which act to return the liquid surface to its equilibrium state. The restoring forces are primarily capillary forces (i.e., surface tension) for surface waves of short wavelength and therefoe larger wavenumbers. The frequency and decay time of these capillary waves are controlled by the surface tension, density, and viscosity of the liquid and by the wavenumber, k defined as $k=2\pi/\lambda$ where $\lambda$ is the wavelength of the wave. Knowledge of the wavenumber, frequency, and decay time of a capillary wave yields information on its controlling viscoelastic parameters.

The waves on an ideal surface, neglecting the effect of the liquid viscosity, propagate with a frequency given by $$\omega^2 = \sigma k^3/\rho$$

where $\sigma$ is the surface tension, k the wavenumber and $\rho$ the liquid density. However, since the fluids examined in practice are not ideal, the propagation of capillary waves on their surfaces are influenced by the liquid viscosity.

For a liquid whose viscosity is relatively low, the capillary waves on the surface propagate before they are ultimately damped by the viscosity of the liquid. The damping coefficient is small relative to the propagation frequency and is defined in the following equation:

$$\Gamma = 2\nu k^2$$

where $\nu$ is the kinematic viscosity.

In contrast, waves on the surface of a high viscosity liquid do not propagate; they are immediately damped by viscous effects. The damping coefficient is given by $$\Gamma = \omega^2/2\nu k^2 = \rho k/2\eta$$

where $\eta$ is the dynamic viscosity.

PHOTON CORRELATION SPECTROSCOPY

The capillary waves that occur at a liquid-liquid or liquid-vapor interface evolve in space and time. Analysis of these waves may be performed in either the time or frequency domains.

Electromagnetic radiation is an important probe of the structure and dynamics of matter. The frequency shift that occurs in light scattered from a medium is a sensitive technique for detecting microscopic motion. Photon correlation spectroscopy probes the fluctuations in the intensity of light that is scattered from moving scatterers. The spectrum of a laser light beam, which has been scattered by a liquid surface, reflects the temporal nature of the surface fluctuations.

Consider the light incident on a fluid interface. The capillary wave on the interface acts as an extremely weak oscillating diffraction grating. Iluminated by the laser beam, it gives rise to a weak diffracted light beam deflected by a small angle ($\Delta\theta$) from the specularly reflected main beam. By use of the proper detection configuration, the scattered beam $I_s$ may be mixed with a specularly reflected reference beam $I_r$, also derived from the laser. This technique of mixing the reference beam $I_r$ and the scattered beam $I_s$ is termed optical mixing. The resulting light intensity detected as output appears as a beat frequency together with a large DC background. The intensity and angle of incidence of the specularly reflected reference beam on the liquid surface is selected to yield the most sensitive mixing ratio.

The detection system includes a photomultiplier tube (PMT) and a pulse amplifier-discriminator (PAD). The photomultiplier tube detects the intensity of light incident upon its photocathode aperture. Each photon detected generates a small signal pulse. The relatively small photon signal (rarely more than 50 mV high and 50 nsec in duration) is converted into a pulse of the proper amplitude and duration for analysis by the signal processor, the correlator. A screening or discrimination of actual signals detected by the PMT due to photons from background noise or instrumental sources is also performed. The device which performs both the discrimination and amplification of the signals received from the PMT is the pulse amplifier-discriminator. The output of the PAD is a TTL level logic pulse for each photon detected by the PMT. Hence the detection system measures the light intensity by counting photons.

The frequency of the surface waves on a liquid is in the kilohertz range. The analysis of the doppler shift in the detected light intensity due to these waves is performed in the time domain by calculating its autocorrelation function. This function, simplistically stated, is the time averaged product of the resultant signal values taken at different points in time. The function appears as a damped cosine wave. The damping effect is due to the viscosity of the liquid. The frequency is a function of the velocity of propagation of the surface wave.

DETAILED DESCRIPTION OF THE INVENTION

What follows is a description of the preferred embodiment of the invention, taken in connection with the accompanying drawings, and its scope will be defined in the appended claims.

DETAILED DESCRIPTION OF THE INVENTION AS ILLUSTRATED IN FIGS. 1 AND 2

Figure 1:
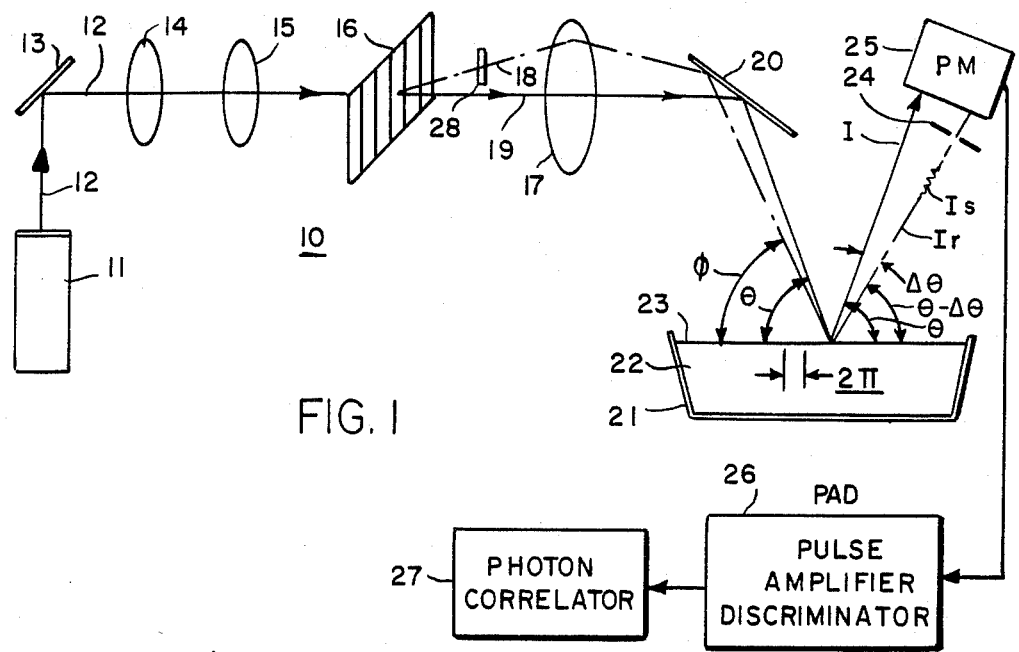
FIG. 1 is a schematic diagram illustrating a PCS system embodying the invention.

Referring now to the drawing and with particular reference to FIG. 1, there is here illustrated a light scattering apparatus adapted for PCS and embodying the invention. The system illustrated is a light scattering, interfacial tension spectrometer. The spectrometer employs PCS to measure the surface tension and viscosity of a liquid by determining the viscoelastic parameters at the interface between the liquid and the adjacent vapor layer.

The spectrometer has a laser source for directing an incident light beam $I_i$ to a reflecting mirror, a series pair of focusing lenses and a diffraction grating. A diffracted, reference light beam $I_r$ is directed through an attenuator and a third, common, diffraction focusing lens to a second mirror. The grating divides the incident beam $I_i$ into the diffracted reference beam $I_r$ and a main, undiffracted, beam $I_m$. The reference beam $I_r$ is angularly displaced from the main beam $I_m$, as shown, to provide an angularly displaced attenuation path and a reflected reference beam from the liquid surface angularly distinct from the reflected main beam. The angle of reflection of the reference beam $I_r$ establishes the same angle at which the scattered light $I_s$ is received to enable heterodyning of the beams $I_r$ and $I_s$.

Both the main and reference beams, $I_m$ and $I_r$, are directed through the common, diffraction, focusing lens to the second mirror. The second mirror directs both of the beams to the surface of a liquid under test. The reflected reference beam $I_r$ and the scattered light $I_s$ are directed through a common aperture, numbered elsewhere as 24, to a photomultiplier tube PM. The PM is coupled to a pulse amplifier-discriminator PAD. The output of the PAD is coupled to a photon correlator.

Thus the spectrometer of the invention is generally indicated at 10. A laser 11 transmits a light beam 12, an incident beam (Ii) to a mirror 13. The beam 12 is directed by the mirror through a pair of convex/convex focusing lenses 14 and 15 to a diffraction grating 16. The incident beam 12 is divided by the grating into a diffracted, reference beam $I_r$ and an undiffrated main beam $I_m$. The beams $I_r$ and $I_m$ are indicated at 18 and 19, respectively. The reference beam $I_r$ is angularly displaced from the beam $I_m$, as shown by the dashed line 18. The beam $I_r$ is directed through an attenuator 28 to adjust its intensity relative to the main beam $I_m$. Both beams are directed through a common, convex-convex, diffraction, forcusing lens 17 to a second mirror 20.

As noted above, the beam $I_r$ is angularly displaced to enable spatial separation from the beam $I_m$. The effective path length of the beam $I_m$ is lengthened by transmitting it through the thickest dimension of the lens 17 along its central axis. In contrast, the deflected reference beam $I_r$ is transmitted through a narrow portion of the lens 17 to maintain precise coherence of the beams $I_m$ and $I_r$, as focused at the image plane of the PM.

Thus, the beam $I_r$, indicated at 18, is directed through an attenuator 18, the narrow portion of the lens 17 to a second mirror 20. The main beam $I_m$, indicated at 19, is transmitted through the central portion of the lens 17 to the mirror 20. The beams 18 and 19 are directed by the mirror 20 to the surface 23 of the liquid under test.

A container 21 holds the liquid 22 under test. The surface 23 of the liquid is indicated as wavelike, having a wavelength of $2\pi/k$, where k is a wave number. The angle of incidence of the beam $I_m$ is $\theta$ and the angle of incidence of the reference beam $I_r$ is $\phi$, or $\theta - \Delta\theta$, as shown. The angle of reflection of the beam $I_m$ is $\theta$ and the reflected angle of the reference beam $I_r$ is $\theta - \Delta\theta$, where $\Delta\theta$ is the angle between the beams $I_m$ and $I_r$, $I_s$, as shown. The scattered beam $I_s$ and the reference beam $I_r$ are directed through an aperture 24 to a photomultiplier tube PM 25. The output of the PM 25 is coupled to a pulse amplifier-discriminator 26. The output of the PAD is coupled to a photon correlator 27.

OPERATION

Figure 2:
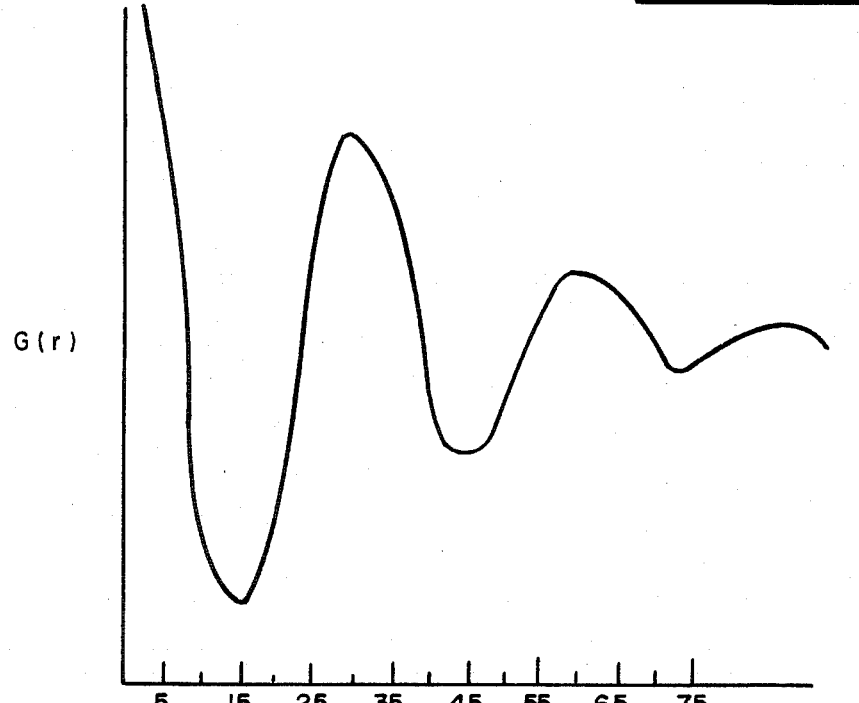
FIG. 2 is a graph of a correlation function G(r) for a selected diffraction grating.

The output of the photon correlator 27 is shown in the graph of FIG. 2 where $G(\tau)$ is the correlation function as a function of time $\tau$.

It will be apparent that the correlation function is a damped cosine function of the form $$G(\tau) \alpha e^{-\Gamma\tau} \cos \omega\tau.$$

As noted above the frequency of the capillary waves propagated at the surface, neglecting viscosity, is defined by $$\omega^2 = \sigma k^3/\rho,$$

where $\sigma$ is the surface tension, k the wave number and $\rho$ the liquid density. The damped correlation function curve is due to the viscosity of the liquid. The damping function is $$\Gamma = 2\sigma k^2,$$

where $\nu$ is the kinematic viscosity.

The frequency of the capillary waves is in the kilohertz range. The analysis of the doppler shift is derived in the time domain by the photon correlator by calculating its autocorrelation function.

The surface tension is derived from the expression:

$$\sigma = \omega^2 \rho/k^3,$$

and the viscosity is derived from the expression $$\nu = \Gamma/2k^2.$$

EXAMPLE

In one series of tests a one milliwatt helium-neon laser was used having a wavelength of 632.8 nm. The grating spacing was chosen to be 1,000 lines per inch. The signal is derived from the light scattered from thermally excited capillary (surface) waves mixed with the local oscillator diffracted, reference beam $I_r$, separated from the main beam $I_m$ by n orders, where n=1, 2 or 3. The temperature at the time was 21.5° C. The experiment was run with various fluids such as water, reservoir oil n-hexane and tar.

The diffraction grating 16 generates a series of light beams in different orders at angles $\theta_n$ from the optical axis in accordance with $$\theta_n = n\lambda/d$$

where n is an integer, $\lambda = 632.8$ nm equals the wavelength of the light and d is the grating spacing, for example, 0.001 inches. Here the beam at $\theta = 0$ is the main beam $I_m$, and is not diffracted.

The lenses 14 and 15 are adjusted to focus the beam $I_r$ to a minimum size at the surface of the photomultiplier. The lenses 14 and 15 are further adjusted to insure that the beams at the position of the attenuator are sufficiently distinct to permit selective attenuation of the diffracted beam.

It is to be noted, as a significant feature, that in the spectrometer illustrated in FIG. 1, no optical elements are placed between the mirror 20, the liquid surface 23 and the photomultiplier 25. The apparatus has been tested over a range of 100-240 centimeters from the mirror 20 to the face of the PM 25.

The lens 17 is adjusted so that all the beams from the diffraction grating 16 are focused to the same plane on the liquid surface 23. After the lens pair 14 and 15 are adjusted to minimize the size of the reflected beam at the PM 25, the mirror 20 is adjusted to direct the desired scattered beam to the PM 25. The aperture 24 is positioned to eliminate undesirable light.

The lens 17 focuses an image of the grating on the surface of the liquid under test and, because of the lens 17, all other beams are, consequently, coincident at that surface. The lens 17 serves to vary the transmission time through the lens as a function of the angle of incident light. Since the main beam $I_m$ has the most direct path, it is effectively slowed down to the minimum, whereas the diffracted beams are slowed down a lessor amount, in order to maintain coherence between the diffracted, reference beam $I_r$, the main beam $I_m$ and the scattered beam $I_s$ at the plane of the PM.

The photon correlator used in this example is a Model 1096 correlator, as manufactured by Langley-Ford of Amherst, Mass. The correlator calculates the autocorrelation function illustrated in FIG. 2. Detailed information on the correlator is available in the instruction manual for the Model 1096, section 2.

As noted above, the autocorrelation function, in essence, is the time averaged product of a signal value at a point in time to a signal value at a later point in time. The autocorrelation function of the light intensity scattered from the surface of a low viscosity liquid is shown in FIG. 2. The function appears as a damped cosine wave. The damping effect is due to the viscosity of the fluid.

DESCRIPTION AND OPERATION OF THE ELECTROPHORESIS APPARATUS IN FIG. 3

Figure 3:
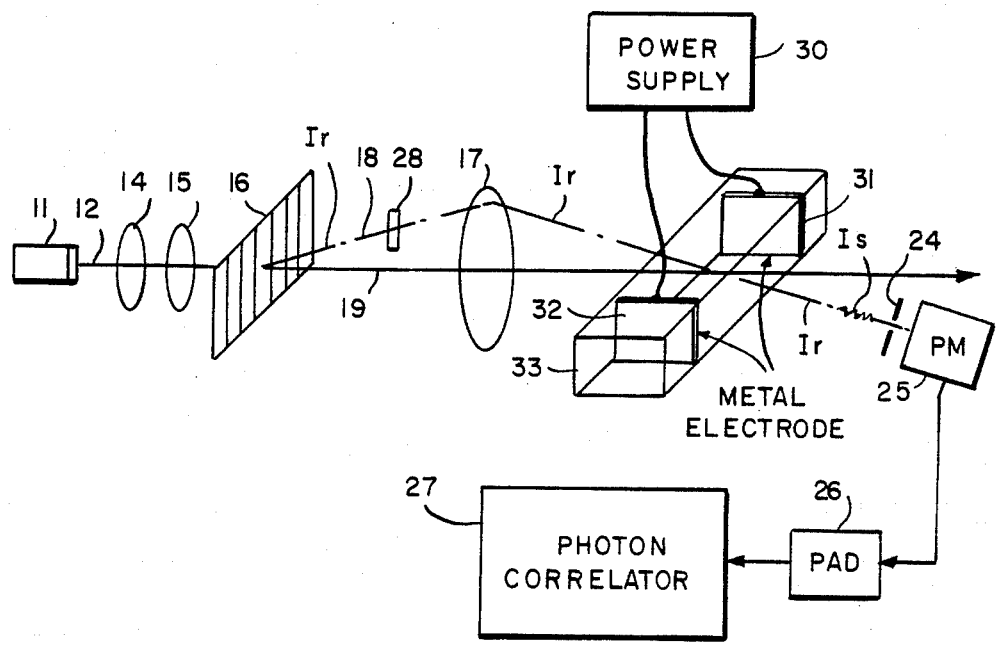
FIG. 3 is a schematic of a modification of the spectrometer in FIG. 1 adapted for eletrophoresis.

Referring now to FIG. 3, there is here illustrated a schematic diagram of a modification of the spectrometer in FIG. 1, adapted for use in electrophoresis. In FIG. 3 like parts in FIG. 1 are referenced with like numerals.

Here again a laser 11 emits a beam 12 through a pair of lenses 14 and 15 to a diffraction grating 16. A main beam $I_m$, indicated at 19, is transmitted through a focusing lens 17 and a transparent cuvette 29. The diffracted reference beam $I_r$, indicated at 18, is transmitted through an attenuator 28, the lens 17 and a sample solution 33 in the cuvette 29. A power supply 30 is coupled to a pair of electrodes 31 and 32 to apply an electric field through the solution 33 under test. Scattered light $I_s$ and the reference beam $I_r$ are directed to the PM 25. The output of the PM is coupled to the pulse amplifier-discriminator 26 and the output of the PAD is coupled to a photon correlator 27. The scattered light $I_s$ has a doppler frequency component which is a function of the charge of the particles moving between the electrodes.

While there has hereinbefore been presented what is, at present, considered to be a preferred embodiment of the invention, it will be apparent that many changes and modifications may be made thereto without departing from the true spirit and scope of the invention. All such changes and modification, therefore, are to be considered within the purview of the invention and form an integral part thereof.

What is claimed is:

1. Apparatus for analyzing properties of liquids by measuring light scattered from said liquid, said apparatus comprising
   (a) means for generating a coherent electromagnetic radiation beam;
   (b) means for dividing said beam into an attenuated reference beam and a main scattering beam, said dividing means disposed between said generating means and a liquid the properties of which are to be measured;
   (c) means for directing and focussing said main scattering beam at a planar region of said liquid to be analyzed;
   (d) means to maintain said scattering beam and said reference beam in substantial coherence as they enter said region to be analyzed;
   (e) means for detecting scattered radiation from said main beam and for detecting non-scattered light from said attenuated reference beam; and
   (f) means for processing said detected radiation for analysis of detected light and thereby for determining selected characteristics of said liquid.

2. The apparatus of claim 1, wherein:
   attenuator means are included after said dividing means for adjusting the intensity of said reference beam relative to said main beam.

3. The apparatus of claim 1, wherein:
   said dividing means includes diffraction grating means.

4. The apparatus of claim 3, wherein:
   means are included for imaging said grating on a surface of said test region.

5. The apparatus of claim 1, wherein:
   means are included for focusing said reference beam spot size at a face of said detecting means.

6. The apparatus of claim 1, wherein:

means are included for focusing said reference and scattered beams on a face of said detecting means.

7. The apparatus of claim 1, wherein:
means are included for generating a diffracted beam from the first said beam.

8. Apparatus as defined in claim 1 forming means to transmit said main beam and said reference beam in substantial coherence, one with the other, to said region to be analyzed, and thence to said detecting and said processing means along a single path.

9. The apparatus as claim 8 wherein said means to maintain said beams in substantial coherence includes a radiation transmission rigid body providing different effective path lengths for said beams through said rigid body.

10. The apparatus of claim 1 wherein said means for generating radiation is a laser.

11. The apparatus of claim 1 wherein said means to maintain said beam in substantial coherence includes a radiation transmission rigid body providing different effective path lengths for said beams through said rigid body.

12. A light scattering, interfacial tension spectrometer, comprising:
(A) a laser for providing a coherent light beam along an optical path;
(B) lens means for focusing said beam;
(C) diffraction means for producing a diffracted, reference beam at an angle relative to said optical path, a main beam being directed along said optical path;
(D) attenuator means for adjusting the intensity of said reference beam relative to said main beam;
(E) a focusing lens means for maintaining the effective path lengths of said reference and main beams equal;
(F) means for directing said main and reference beams to a surface having thermally excited capillary waves;
(G) means for detecting and heterodyning said reference beam and scattered light from said surface;
(H) amplifier-discriminator means for amplifying and discriminating a signal from said detector means; and
(I) photon correlator means for producing a correlation function from which the surface tension and viscosity of the fluid under test may be derived.

13. The method of measuring the surface tension and viscosity of a fluid under test, comprising:
(A) generating a light beam;
(B) focusing said beam to provide a minimum spot size at an image plane associated with photodetection;
(C) dividing said beam to produce a reference beam and higher order diffracted beams;
(D) focusing said diffracted and reference beams on a fluid surface;
(E) detecting the reflected and scattered beams from said surface to provide a signal indicative of the thermally excited capillary waves of said surface;
(F) amplifying and discriminating said signal to extract it from noise; and
(G) autocorrelating said amplified signals to provide an output signal indicative of the surface tension and viscosity of said fluid.

14. A light scattering, electrophoresis apparatus, comprising:
(A) means for generating an electromagnetic radiation beam;
(B) means for dividing said beam into a reference beam and a main beam;
(C) means for maintaining said reference and main beams substantially in coherence relative to each other;
(D) means transparent to said radiation beams for containing a solution in a region under test;
(E) means for applying an electric field through said solution;
(F) means for directing said cohered beams into said test solution, said dividing means being disposed in a radiation path between said generating means and test region;
(G) means for detecting reflected radiation from said reference beam and for detecting scattered radiation from said region; and
(H) means for processng said detected radiation for determining seleceted characteristics of moving charged particles in said region under test.

15. The apparatus of claim 14, wherein:
means are included for imaging said dividing means within the volume of said test solution.

16. The apparatus of claim 14, wherein:
said radiation generator is a laser.

17. The apparatus of claim 16, wherein:
(A) said dividing means is a diffraction grating;
(B) means are included for imaging said diffraction grating within the volume of said test solution;
(C) said relative coherence means includes a light transmissive, rigid body providing differing effective path lengths for said beams through said rigid body; and
(D) attenuator means are included after said diffraction grating for adjusting the intensity of said reference beam relative to said main beam.

* * * * *